United States Patent [19]

Böhm et al.

[11] Patent Number: 5,852,051
[45] Date of Patent: Dec. 22, 1998

[54] DIPEPTIDE P-AMIDINOBENZYLAMIDES WITH N-TERMINAL SULFONYL OR AMINOSULFONYL RADICALS

[75] Inventors: Hans-Joachim Böhm, Limburgerhof; Stefan Koser; Helmut Mack, both of Ludwigshafen; Thomas Pfeiffer, Böhl-Iggelheim; Werner Seitz, Plankstadt; Hans Wolfgang Höffken, Ludwigshafen; Wilfried Hornberger, Neustadt; Thomas Zierke, Böhl-Iggelheim, all of Germany

[73] Assignee: BASF Aktiengesellschaft, Ludwigshafen, Germany

[21] Appl. No.: 849,364

[22] PCT Filed: Nov. 25, 1995

[86] PCT No.: PCT/EP95/04646

§ 371 Date: Jun. 5, 1997

§ 102(e) Date: Jun. 5, 1997

[87] PCT Pub. No.: WO96/17860

PCT Pub. Date: Jun. 13, 1996

[30] Foreign Application Priority Data

Dec. 6, 1994 [DE] Germany ............ 44 43 390.5

[51] Int. Cl.[6] .............. A61K 31/40; A61K 31/445; C07D 207/00; C07D 401/00

[52] U.S. Cl. ............... 549/423; 514/422; 514/317; 514/343; 548/540; 548/527; 546/208; 546/279.1

[58] Field of Search .............. 548/527, 540; 514/423, 422, 317, 343; 546/208, 279.1

[56] References Cited

FOREIGN PATENT DOCUMENTS

| 601 459 | 6/1994 | European Pat. Off. . |
| 669 317 | 8/1995 | European Pat. Off. . |
| 672 658 | 9/1995 | European Pat. Off. . |
| 93/11152 | 6/1993 | WIPO . |
| 94/29336 | 12/1994 | WIPO . |

*Primary Examiner*—Deborah C. Lambkin
*Attorney, Agent, or Firm*—Keil & Weinkauf

[57] ABSTRACT

Compounds of the formula I

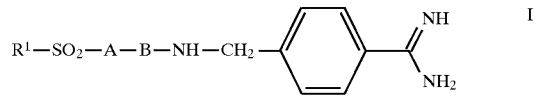

in which $R^1$, A and B have the meanings stated in the description, and the preparation thereof are described. The novel compounds are suitable for controlling diseases.

5 Claims, No Drawings

DIPEPTIDE P-AMIDINOBENZYLAMIDES WITH N-TERMINAL SULFONYL OR AMINOSULFONYL RADICALS

This application is a 371 of PCT/E95/04646 filed Nov. 25, 1995.

The present invention relates to dipeptide p-amidinobenzylamides with N-terminal sulfonyl or aminosulfonyl radicals, to the preparation thereof and to the use thereof as thrombin inhibitors.

EP 601 459 describes heterocyclic thrombin inhibitors which have a sulfonamide group.

The present invention relates to compounds of the formula I $$R^1-SO_2-A-B-NH-CH_2-\text{(p-amidinophenyl)} \quad \text{I}$$

and their stereoisomers and their salts with physiologically tolerated acids, in which the substituents have the following meanings:

$R^1$ is $C_1$–$C_{20}$-alkyl, $C_1$–$C_3$-fluoroalkyl, $C_3$–$C_8$-cycloalkyl, aryl-$C_1$–$C_{10}$-alkyl, aryl, hetaryl, OH or $R^3R^2N$ where $R^2$ and $R^3$ are identical or different and are hydrogen, $C_1$–$C_{10}$-alkyl, aryl, aryl-$C_1$–$C_{10}$-alkyl or together are a $C_2$–$C_7$-alkylene chain to which an aryl or hetaryl radical can be fused or which can contain a hetero atom (O, S, NH or substituted N), A is an α-amino acid residue of the formula II $$-NH-\underset{\underset{R^5}{|}}{\overset{\overset{R^4}{|}}{C}}-CO- \quad \text{II}$$

where $R^4$ is hydrogen, $C_1$–$C_8$-alkyl, $C_3$–$C_7$-cycloalkyl, aryl or aryl-$C_1$–$C_3$-alkyl, $R^5$ is hydrogen, $C_1$–$C_8$-alkyl, $C_3$–$C_7$-cycloalkyl, $C_3$–$C_7$-cycloalkyl-$C_{1-3}$-alkyl, aryl, aryl-$C_1$–$C_3$-alkyl, di($C_3$–$C_7$-cycloalkyl)-methyl or diphenylmethyl or—if $R^4$=H—a $C_1$–$C_8$-alkyl radical in which one hydrogen atom is replaced by $OR^6$ or CO—$OR^6$ ($R^6$=hydrogen, $C_1$–$C_8$-alkyl or aryl-$C_{1-C_3}$-alkyl), or $R^4$ and $R^5$ together are a $C_2$–$C_6$-alkylene chain, which may contain a fused-on aryl radical, B is a cyclic α-amino acid residue of the formula III $$-N\underset{\underset{O}{\|}}{\overset{\phantom{x}}{\phantom{x}}}(CH_2)_m \quad \text{III}$$

where m is 2, 3 or 4, and one hydrogen on the ring can be replaced by a hydroxyl or $C_1$–$C_3$-alkyl group and—if m=3 or 4—a $CH_2$ group in the ring can be replaced by oxygen, sulfur, NH— or N-$C_1$–$C_4$-alkyl and/or two adjacent hydrogen atoms can be replaced by a double bond.

The following four groups of compounds are preferred:

1. Compounds of the formula I, in which the substituents have the following meanings:

$R^1$ OH or $R^3R^2N$, wwhere $R^2$ and $R^3$ are identical or different and are hydrogen, $C_1$–$l_0$-alkyl, aryl, aryl-$C_1$–$C_{10}$-alkyl or together are a $C_2$–$C_7$-alkylene chain to which an aryl or hetaryl radical may be fused or which may contain a hetero atom (O, S, NH or substituted N), A an α-amino acid residue of the formula II $$-NH-\underset{\underset{R^5}{|}}{\overset{\overset{R^4}{|}}{C}}-CO- \quad \text{II}$$

where $R^4$ is hydrogen, $C_1$–$C_8$-alkyl, $C_3$–$C_7$-cycloalkyl, aryl or aryl-$C_{1-C_3}$-alkyl, $R^5$ is hydrogen, $C_1$–$C_8$-alkyl, $C_3$–$C_7$-cycloalkyl, $C_3$–$C_7$-cycloalkyl-$C_{1-3}$-alkyl, aryl, aryl-$C_1$–$C_3$-alkyl, di($C_3$–$C_7$-cycloalkyl)-methyl or diphenylmethyl or—if $R^4$=H—a $C_1$–$C_8$-alkyl radical in which one hydrogen atom is replaced $OR^6$ or CO—$OR^6$ ($R^6$=hydrogen, $C_1$–$C_8$-alkyl or aryl-$C_1$–$C_3$-alkyl), or $R^4$ and $R^5$ together are a $C_2$–$C_6$-alkylene chain which may contain a fused-on aryl radical, B is cyclic α-amino acid residue of the formula III $$-N\underset{\underset{O}{\|}}{\overset{\phantom{x}}{\phantom{x}}}(CH_2)_m \quad \text{III}$$

where m is 2, 3 or 4, and one hydrogen atom on the ring can be replaced by a hydroxyl or $C_1$–$C_3$-alkyl group and —if m=3 or 4—one $CH_2$ group in the ring can be replaced by oxygen, sulfur, NH— or N-$C_1$–$C_4$-alkyl and/or two adjacent hydrogen atoms can be replaced by a double bond.

2. Compounds of the formula I in which the substituents have the following meanings:

$R^1$ $C_1$–$C_{20}$-alkyl, $C_1$–$C_3$-fluoroalkyl, $C_3$–$C_8$-cycloalkyl, aryl-$C_1$–$C_{10}$-alkyl, aryl or hetaryl, A an α-amino acid residue of the formula II $$-NH-\underset{\underset{R^5}{|}}{\overset{\overset{R^4}{|}}{C}}-CO- \quad \text{II}$$

where $R^4$ is $C_1$–$C_8$-alkyl, $C_3$–$C_7$-cycloalkyl, aryl or aryl-$C_1$–$C_3$-alkyl, $R^5$ is $C_1$–$C_8$-alkyl, $C_3$–$C_7$-cycloalkyl, $C_3$–$C_7$-cycloalkyl-$C_{1-3}$-alkyl, aryl, aryl-$C_1$–$C_3$-alkyl, di($C_3$–$C_7$-cycloalkyl)-methyl or diphenylmethyl or $R^4$ and $R^5$ together are a $C_2$–$C_6$-alkylene chain which may contain a fused-on aryl radical, B one of the radicals

[structural formulas of various heterocyclic B radicals]

3. Compounds of the formula I in which the substituents have the following meanings:

$R^1$ $C_1$–$C_{20}$-alkyl, $C_1$–$C_3$-fluoroalkyl, $C_3$–$C_8$-cycloalkyl, aryl-$C_1$–$C_{10}$-alkyl, aryl, hetaryl or OH, A an α-amino acid residue of the formula

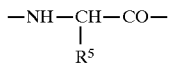

where
$R^5$ is a $C_1$–$C_8$-alkyl radical in which one hydrogen atom is replaced by $OR^6$ or CO—$OR^6$ ($R^6$=hydrogen, $C_1$–$C_8$-alkyl or aryl-$C_1$–$C_3$-alkyl), B one of the radicals

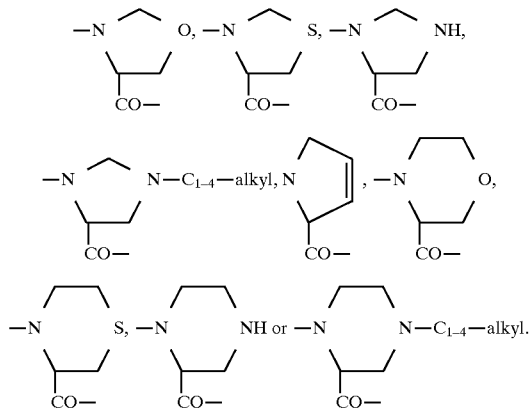

4. Compounds of the formula I in which the substituents have the following meanings:

$R^1$ $C_1$–$C_{20}$-alkyl, $C_1$–$C_3$-fluoroalkyl, $C_3$–$C_8$-cycloalkyl, aryl-$C_1$–$C_{10}$-alkyl, aryl, hetaryl or OH, A an α-amino acid residue of the formula

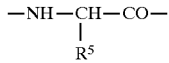

where
$R^5$ a $C_1$–$C_8$-alkyl radical in which one hydrogen atom is replaced by $OR^6$ or CO—$OR^6$ ($R^6$=hydrogen or $C_1$–$C_8$-alkyl), B a cyclic α-amino acid residue of the formula III

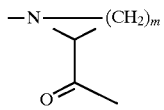

where m is 2, 3 or 4, and one hydrogen on the ring is replaced by a hydroxyl or $C_1$–$C_3$-alkyl group.

The term "aryl" means mono- or bicyclic aromatic groups which contain 6 to 10 carbon atoms in the ring system, eg. phenyl or naphthyl, and may have up to three identical or different substituents.

The term "hetaryl" refers to 5- or 6-membered aromatic rings which can contain 1 or 2 hetero atoms such as N, O or S and to which an aryl ring may be fused.

In groups 1–4 of compounds I, particular mention may be made of compounds with the following substituents $R^1$, A and B:

Compound group 1
$R^1$ $NH_2$, $C_{1-4}$-mono- or dialkylamino or piperidinyl
A residues of the amino acids valine, leucine, isoleucine, phenylglycine, cyclohexylglycine, phenylalanine, cyclohexylalanine, diphenylalanine, dicyclohexylalanine, where phenyl rings present in the residues may be substituted by up to three identical or different $C_{1-4}$-alkyl-, $C_{1-4}$-alkoxy, OH, F, Cl or $COOR^6$ groups
B residues of the amino acids azetidine-2-carboxylic acid, proline, pipecolic acid, dehydroproline, 4-hydroxyproline, oxaproline, thiaproline, 4-$C_{1-4}$-alkylpipecolic acid, morpholine-2-carboxylic acid, piperazine-2-carboxylic acid, 4-$C_{1-4}$-alkylpiperazine-2-carboxylic acid Compound group 2
$R^1$ $C_{1-4}$-alkyl, $CF_3$—$CH_2$—, phenyl, naphthyl, phenyl-$C_{1-4}$-alkylene [sic] (particularly benzyl and phenethyl), naphthyl-$C_{1-4}$-alkylene [sic], pyridyl, isoquinolyl
A residues of the amino acids α-methylphenylalanine, α-methylcyclohexylalanine, α-methylphenylglycine, α-methylcyclohexylglycine
B residues of the amino acids dehydroproline, oxaproline, thiaproline, pipecolic acid, 4-$C_{1-4}$-alkylpipecolic acid, morpholine-2-carboxylic acid, piperazine-2-carboxylic acid, 4-$C_{1-4}$-alkyl-piperazine-2-carboxylic acid Compound group 3
$R^1$ $C_{1-4}$-alkyl, $CF_3$—$CH_2$—, phenyl, naphthyl, phenyl-$C_{1-4}$-alkylene (especially benzyl and phenethyl), naphthyl-$C_{1-4}$-alkylene, pyridyl, isoquinolyl
A residues of the amino acids aspartic acid, glutamic acid, serine, homoserine, threonine, where the non-linked carboxylic acid or hydrogxyl group can be esterified or etherified, respectively, by a $C_{1-8}$-alkyl radical (especially t-butylserine aund t-butylthreonine)
B residues of the amino acids dehydroproline, oxaproline, thiaproline, morpholine-2-carboxylic acid Compound group 4
$R^1$ $C_{1-4}$-alkyl, $CF_3$—$CH_2$—, phenyl, naphthyl, phenyl-$C_{1-4}$-alkylene [sic] (especially benzyl and phenethyl), naphthyl-$C_{1-4}$-alkylene [sic], pyridyl, isoquinolyl
A residues of the amino acids serine, homoserine, threonine, in which the OH group can be etherified by $C_{1-8}$-alkyl, or aspartic acid, glutamic acid, in which the non-linked carboxylic acid can be esterified by $C_{1-8}$-alkyl
B residues of the amino acids 4-hydroxyproline, 4-$C_{1-4}$-alkylpipecolic acid The radicals $R^1$, A and B are, as depicted in structure I, linked together, and the amino acid residues in a preferably have the (D) configuration and the amino acid residues in B preferably have the (L) configuration.

The following substances may be mentioned as preferred:
$CF_3$—$CH_2$—$SO_2$-(D)Phe-Pro-NH-pAmb
$C_4H_9$—$SO_2$-(D)Phe-Pro-NH-pAmb
$C_8H_{17}$—$SO_2$-(D)Phe-Pro-NH-pAmb
$C_{16}H_{33}$—$SO_2$-(D)Phe-Pro-NH-pAmb
i-Propyl-$SO_2$-(D)Phe-Pro-NH-pAmb
Phenyl-$SO_2$-(D)Phe-Pro-NH-pAmb
2-Naphthyl-$SO_2$-(D)Phe-Pro-NH-pAmb
3-Pyridyl-$SO_2$-(D)Phe-Pro-NH-pAmb
2-Thienyl-$SO_2$-(D)Phe-Pro-NH-pAmb
N-Piperidinyl-$SO_2$-(D)Phe-Pro-NH-pAmb
$H_2$N—$SO_2$-(D)Phe-Pro-NH-pAmb
$Me_2$N-$SO_2$-(D)Phe-Pro-NH-pAmb
EtHN-$SO_2$-(D)Phe-Pro-NH-pAmb
Me-$SO_2$-(D)Phe(4-OMe)-Pro-NH-pAmb
Me-$SO_2$-(D)Phe(3-OMe)-Pro-NH-pAmb
Me-$SO_2$-(D)Phe(2-Cl)-Pro-NH-pAmb
Me-$SO_2$-(D)Dpa-Pro-NH-pAmb
Me-$SO_2$-(L)Dpa-Pro-NH-pAmb
Me-$SO_2$-(D)Dpa(4,4'-OMe)-Pro-NH-pAmb
Me-$SO_2$-(L)Dpa(4,4'-OMe)-Pro-NH-pAmb
Me-$SO_2$-(D)Dpa(4,4'-Cl)-Pro-NH-pAmb
Me-$SO_2$-(L)Dpa(4,4'-Cl)-Pro-NH-pAmb Me-SO$_2$-(D,L)Phg(3,4-Cl)-Pro-NH-pAmb Me-SO$_2$-(D)Asp(OH)-Pro-NH-pAmb Me-SO$_2$-(L)Asp(OH)-Pro-NH-pAmb Me-SO$_2$-(D)Asp(OMe)-Pro-NH-pAmb Me-SO$_2$-(L)Asp(OMe)-Pro-NH-pAmb Me-SO$_2$-(D)Asp(OtBu)-Pro-NH-pAmb Me-SO$_2$-(L)Asp(OtBu)-Pro-NH-pAmb Me-SO$_2$-(D)Phe-Aze-NH-pAmb Me-SO$_2$-(D)Phe-Pip-NH-pAmb 1-Naphthyl-SO$_2$-Gly-Pro-NH-pAmb The abbreviations used in this list have the following meanings:

Phe=phenylalanine, pAmb=p-amidinobenzyl, Pro=proline,

Cpa=diphenylalanine, Phg=phenylglycine, Asp=aspartic acid,

Aze=azetidine-2-carboxylic acid, Pip=pipecolic acid

The compounds of the formula I may exist as such or be in the form of their salts with physiologically tolerated acids. Examples of such acids are: hydrochloric acid, citric acid, tartaric acid, lactic acid, phosphoric acid, methanesulfonic acid, acetic acid, formic acid, maleic acid, fumaric acid, maleic [sic] acid, succinic acid, hydroxysuccinic acid, sulfuric acid, glutaric acid, aspartic acid, pyruvic acid, benzoic acid, glucuronic acid, oxalic acid, ascorbic acid and acetylglycine.

The invention furthermore relates to the intermediates of the formula IV

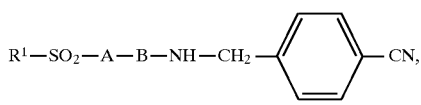

where $R^1$, A and B have the stated meanings, which can be used to prepare the compounds I.

The compounds I can be prepared starting from the α-amino acid H—A—OH or from the N-protected cyclic amino acid B—OH in accordance with Reaction Scheme I or II.

Scheme I

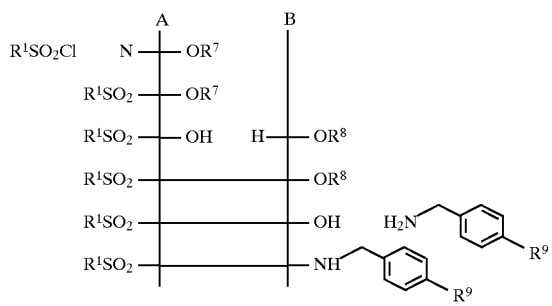

Scheme II

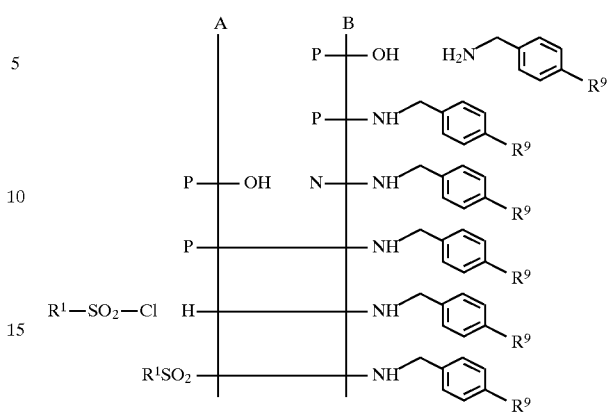

In the above reaction schemes, $R^7$ is H or $C_1$–$C_4$-Alkyl, $R^8$ is $C_1$–$C_4$-alkyl, preferably methyl or t-butyl, $R^9$ is CN or

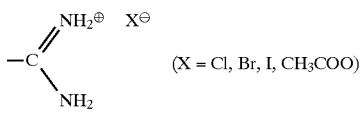

(X = Cl, Br, I, CH$_3$COO)

and P is a protective group, preferably t-butoxycarbonyl (Boc) or benzyloxycarbonyl (Cbz).

Alternatively, the protected amino acids P—A—OH and H—B—OR$^8$ can be coupled to give the dipeptide P—A—B—OR$^8$ and subsequently reacted after elimination of P with $R^1SO_2Cl$ or of $R^8$ with p-cyano- or p-amidinobenzylamine, any reaction sequence being possible.

$R^1$—SO$_2$—A—OH can also be coupled directly with para-H-B-NHCH$_2$C$_6$H$_4$R$^9$ to give the final product I or intermediate IV.

The required coupling reactions are carried out under standard conditions of peptide chemistry (see M. Bodansky, A. Bodansky "The Practice of Peptide Synthesis", Springer Verlag, 1084 [sic]).

Boc protective groups are eliminated with HCl/dioxane or CF$_3$COOH/methylene chloride, and Cbz protective groups are eliminated by hydrogenolysis or with HF. Ester functionalities are hydrolyzed with NaOH or LiOH in an alcoholic solvent such as methanol or ethanol. t-Butyl esters are hydrolyzed with acids, eg. CF$_3$COOH.

The reaction with the sulfonyl chlorides $R^1$—SO$_2$Cl in the presence of an organic base such as triethylamine, pyridine or N,N-diiso-propylethylamine takes place in organic solvents such as CH$_2$C$_2$, THF or DMF. In the case of free carboxylic acid functionalities, the reaction is carried out in the presence of aqueous alkali metal hydroxide or carbonate solutions.

The amidines are prepared from the nitrile precursors by the classical Pinner synthesis (R. Roger and D. G. Neilson, Chem. Rev. 61, 1961, 179) or, preferably, by modification of the Pinner synthesis which proceeds via imino thioester salts as intermediate (H. Vieweg et al., Pharmazie 39, 1994, 226). Catalytic hydrogenation of N-hydroxyamidines, which can be obtained by addition of hydroxylamine onto the cyano group, with Raney Ni or Pd/C in alcoholic solvents likewise results in amidines (B. J. Broughton et al., J. Med. Chem. 18, 1975, 1117).

The novel compounds can be used for the therapy and prophylaxis of all diseases in which thrombin is involved.

These are, in particular, thromboembolic disorders such as myorcardial infarct, peripheral arterial occlusive disease, deep vein thrombosis, pulmonary embolism and stroke. In addition, they can be used to prevent reocclusion after opening of arterial vessels by mechanical methods or lysis.

Their particular advantage is that they are also effective after oral administration.

The compounds according to the invention can be administered orally or parenterally in a conventional way (subcutaneously, intravenously, intramuscularly, intraperitoneally, rectally). Administration can also take place with vapors or sprays through the nasopharyngeal space.

The dosage depends on the age, condition and weight of the patient and on the mode of administration. As a rule, the daily dose of active substance per person is about 10–2,000 mg on oral administration and about 1–200 mg on parenteral administration. This dose can be given in 2 to 4 single doses or once a day as depot form.

The novel compounds can be used in conventional solid or liquid pharmaceutical forms, eg. as uncoated or (film-) coated tablets, capsules, powders, granules, suppositories, solutions, ointments, creams or sprays. These are produced in a conventional way. In these, the active substances can be processed with conventional pharmaceutical aids such as tablet binders, fillers, preservatives, tablet disintegrants, flow regulators, plasticizers, wetting agents, dispersants, emulsifiers, solvents, release-slowing agents, antioxidants and/or propellant gases (cf. H. Sucker et al: Pharmazeutische Technologie, Thieme-Verlag, Stuttgart, 1978). The administration forms obtained in this way normally contain the active substance in an amount of from 0.1 to 99% by weight.

EXAMPLE 1

N-Isopropylsulfonyl-D-phenylalanylproline (p-amidinobenzyl)amide acetate a) Boc-D-Phenylalanylproline (p-cyanobenzyl)amide 2.0 g (14.6 mmol) of isobutyl chloroformate were added in 2 min to a solution of 5.1 g (14.2 mmol) of Boc-D-Phe-Pro-OH and 1.53 g (15.2 mmol) of N-methylmorpholine in 15 ml of DMF at −15° C., the mixture was stirred for 10 min and then a solution of 1.9 g (14.2 mmol) of p-cyanobenzylamine (W. Walter et al., Ann. 660, 1962, 60) and 1.53 g of N-methylmorpholine in 3 ml of DMF was added. After stirring at −15° C. for 3 h, a TLC check ($CH_2Cl_2$/MeOH, 9/1) showed no detectable starting compounds.

For isolation, the reaction mixture was poured into 200 ml of water, when an oil separated out and, after a short time, solidifed and was broken up and filtered off with suction. The still moist residue was dissolved in a mixture of 250 ml of ethyl acetate and 50 ml of ether and washed successively with a 5% strength aqueous citric acid, bicarbonate and saturated sodium chloride solutions. After drying over $Na_2SO_4$, the solvent was removed by distillation under reduced pressure, and the residue was mixed with n-hexane and then filtered off with suction. Recrystallization from 50 ml of ethyl acetate afforded 5.6 g of TLC-pure product, m.p. 156°–157° C.

b) D-Phenylalanylproline (p-cyanobenzyl)amide hydrochloride

The above compound was dissolved in 100 ml of 5N HCl in dioxane and stirred at room temperature for 3 h, during which the hydrochloride precipitated. This was filtered off with suction, washed with ether until free of HCl and dried over KOH under reduced pressure. 4.6 g (95% of theory) of white crystals, m.p. 220°–222° C., were obtained.

c) N-Isopropylsulfonyl-D-phenylalanylproline (p-cyanobenzyl)-amide 2.05 g (6.05 mmol) of the above hydrochloride were suspended in 50 ml of $CH_2Cl_2$. Addition of 1.35 g (13.5 mmol) of triethylamine resulted in a solution to which, at 0°–5° C., 0.9 g (6.1 mmol) of propane-2-sulfonyl chloride dissolved in 10 ml of $CH_2Cl_2$ was added dropwise. The reaction mixture was stirred at room temperature for 5 h and then extracted by shaking with water, 5% strength citric acid and 5% strength $NaHCO_3$ solution. After drying over $Na_2SO_4$ and removing the solvent by distillation, the viscous oily residue was recrystallized from an ethyl acetate/ether mixture (1:1).

d) N-Isopropylsulfonyl-D-phenylalanylproline (p-thioamidinobenzyl)amide 4.1 g of the above compound and 4 ml of triethylamine were dissolved in 40 ml of pyridine, saturated with $H_2S$ at 0° C. and left to stand at room temperature overnight. A TLC check ($CH_2Cl_2$/MeOH, 9/1) showed that the conversion to thioamide was complete. For isolation, the pyridine was substantially removed by distillation under reduced pressure, and the residue was taken up in 250 ml of ethyl acetate and washed with sodium chloride, 5% strength citric acid and $NaHCO_3$ solutions. Drying and removal of the solvent by distillation resulted in 4.1 g of pure crystalline thioamide.

e) N-Isopropylsulfonyl-D-phenylalanylproline (p-amidinobenzyl)amide acetate

The thioamide was dissolved in 150 ml acetone and, after addition of 7 ml of methyl iodide, left to stand at room temperature overnight. The amorphous residue after the solvent had been stripped off was stirred with dry ether and then dried. The methyl S-methylthioimidate hydroiodide was dissolved in 50 ml of ethanol, 15 ml of 10% ammonium acetate solution were added, and the mixture was heated at 60° C. for 3 h. For isolation, the solvent was stripped off, the residue was dissolved in 100 ml of $CH_2Cl_2$, the insoluble constituents were removed by filtration, and then the $CH_2Cl_2$ was removed by distillation. Digestion with an ethyl acetate/diethyl ether mixture was carried out to remove the impurities soluble therein. The remaining iodide/acetate mixed salt was dissolved in acetone/water (3/2) and converted by means of an IRA acetate ion exchanger into the pure acetate which, after heating in acetonitrile, was in the form of a white crystalline powder, m.p. 148°–152° C. (decomposition). FAB-MS $(M+H)^+$=500.

EXAMPLE 2

N-(Thienyl-2-sulfonyl)-D-phenylalanylproline (p-amidinobenzyl)amide acetate a) Boc-D-phenylalanylproline (p-amidinobenzyl)amide Boc-D-Phenylalanylproline (p-cyanobenzyl)amide (see Example 1a for preparation) was converted by method 1c using $H_2S$ into the thioamide and then as in 1d into the amidine.

The amidine was obtained in the form of white crystals, m.p. 237°–239° C. FAB-MS $(M-H)^+$=347.

b) D-Phenylalanylproline (p-amidinobenzyl)amide dihydrochloride

The Boc protective group was eliminated from the above compound with 5N HCl in dioxane as in Example 1b. The dihydrochloride was isolated as a very hygroscopic powder, m.p. 130°–140° C., FAB-MS $(M-H)^+$=247.

c) N-(Thienyl-2-sulfonyl)-D-phenylalanylproline (p-amidinobenzyl)amide acetate

A solution of 3.9 g (12.6 mmol) of N-phenylsulfonyl-D-phenyl-alanine (Egypt. J. Chem. 23, 1981, 273) in 40 ml of THF was, after addition of 1.9 g (12.6 mmol) of 1-hydroxybenzotriazole and 3.3 g (25 mmol) of dicyclohexylcarbodiimide, stirred at room temperature for 4 h. The precipitated urea was filtered off with suction and washed with a little THF.

To this filtrate was added, at 5° C., a solution of 4.1 g (12.6 mmol) of N-(p-amidinobenzyl)prolinamide dihydrochloride and 1.6 g of sodium bicarbonate in 6 ml of water. After stirring at room temperature for 48 h, the solvent was substantially removed by distillation, the residue was taken up in ethanol, filtered to remove insolubles and again concentrated.

The residue was purified on a solica gel column with a $CH_2Cl_2$ (MeOH/50% strength acetic acid mixture (45/5/1.5). The eluate of pure fractions was distilled, adding toluene towards the end, and the residue was recrystallized from 50 ml of acetone with addition of a little water. 3.3 g (48% of theory) of amidine acetate were isolated in the form of white crystals, m.p. 95°–98° C. FAB-MS $(M-H)^+$=540.5.

EXAMPLE 3

N-(2-Naphthylsulfonyl)-D-phenylalanylproline (p-amidinobenzyl)amide acetate a) Boc-Proline (p-cyanobenzyl)amide 276 g of Boc-Pro-OSu (0.88 mol) were introduced into 2 l of methylene chloride at 0° C. To this solution were added successively 163.9 g of 4-cyanobenzylamine hydrochloride (0.97 mol) and 230 ml of diisopropylethylamine (1.34 mol). The suspension was stirred in a melting ice bath for 48 h and then filtered. The filtrate was extracted with 20% strength $NaHSO_4$ solution (4×), saturated $NaHCO_3$ solution (3×) and saturated sodium chloride solution (2×), dried and evaporated in a rotary evaporator. Recrystallization of the residue from methyl tert-butyl ether resulted in isolation of 261 g (90%) of white crystals, m.p. 124°–125° C.

b) N-(4-Cyanobenzyl)prolinamide hydrochloride 260 g (0.79 mol) of the above Boc-protected compound were dissolved in 1 liter of diethyl ether and, after addition of an excess of ethereal HCl solution, stirred overnight. The precipitated hydrochloride was filtered off, washed with diethyl ether until free of HCl and then recrystallized from ethanol. 200 g (95%) of white crystals were obtained, m.p. 209°–211° C.

c) N-(2-Naphthylsulfonyl)-D-phenylalanylproline (p-cyanobenzyl)amide 5.9 g (21.3 mmol) of the above proline amide hydrochloride were dissolved in 100 ml of DMF and successively 7.8 g (21.3 mmol) of N-(2-naphthylsulfonyl)-D-phenylalanine (A. Bernat et al., FR 2593812), 2.15 g (21.3 mmol) of triethylamine and 3.25 g (21.3 mmol) 1-hydroxybenzotriazole (HOBT) were added. While stirring at 0°–5° C., a solution of 4.4 g (21.3 mmol) of dicyclohexylcarbodiimide in 30 ml of ethyl acetate was added, and the mixture was then stirred at room temperature for 48 h.

The precipitated urea was filtered off with suction and then the solvent was substantially removed by distillation under reduced pressure, and the residue was taken up in 200 ml of ethyl acetate and washed successively with 5% strength $NaHCO_3$ solution, 4% strength citric acid solution and water. After drying and removal of the ethyl acetate by distillation, the oily residue was dissolved in 30 ml of $CH_2Cl_2$ and crystallized by adding 50 ml of ether. 9.1 g (76%) of the required compound was isolated.

d) N-(2-Naphthylsulfonyl)-D-phenylalanylproline (p-amidinobenzyl)amide acetate

With exclusion of moisture, 80 ml of methanol were saturated at 0° C. with Hcl [sic] gas, 5.6 g (10 mmol) of the above compound were dissolved therein, and the solution was left to stand at 0° C. for 48 h. The solvent was then stripped off at 20° C., and the residue was dissolved in 20 ml of methanol and added at 0°–5° C. to 80 ml of $NH_3$-saturated methanol solution. The solution was refluxed for 3 h and then cooled and filtered, the solvent was removed by distillation, and the residue was converted into the amidine acetate using an acetate ion exchanger. Recrystallization from acetone with the addition of a little water resulted in 5.1 g (80%) of the title compound as white crystals, m.p. 221°–225° C., FAB-MS $(M+H^+)$=584.5.

EXAMPLE 4

N-(Pyridyl-3-sulfonyl)-D-phenylalanylproline (p-amidinobenzyl)amide acetate a) N-(Pyridyl-3-sulfonyl)-D-phenylalanylproline (p-cyanobenzyl)amide D-Phenylalanylproline (p-cyanobenzyl)amide hydrochloride (preparation similar to 1a and b) was reacted as in Example 1c with pyridin-3-sulfonyl chloride. $R_F$=0.57 ($CH_2Cl_2$/MeOH, 9/1).

b) N-(Pyridyl-3-sulfonyl)-D-phenylalanylproline (p-hydroxyamidinobenzyl)amide acetate 2 g of the above compound, 0.74 g of hydroxylamine hydrochloride and 2.2 g of triethylamine were dissolved in 30 ml of ethanol and stirred under nitrogen at 60°–70° C. for 2 h. A TLC check then showed that no starting material was detectable. Water was added to the reaction mixture, and the pH was adjusted to 3–4 with glacial acetic acid. The aqueous phase was extracted several times with $CH_2Cl_2$, the combined $CH_2Cl_2$ extracts were dried and the methylene chloride was removed by distillation. The residue, which still contained acetic acid, was used directly in the next reaction. $R_F$=0.1 ($CH_2Cl_2$/MeOH, 9/1).

c) N-(Pyridyl-3-sulfonyl)-D-phenylalanylproline (p-amidinobenzyl)amide acetate

A solution of 2.4 g (5 mmol) of the above compound in 40 ml of methanol was hydrogenated in the presence of 0.4 g of 10% Pd/carbon at 50° C. for 7 h. The catalyst was then filtered off with suction, the solvent was removed by distillation, and the residue was mixed with ethyl acetate and heated. A clear solution was produced by adding acetone and a little water and, on cooling, the amide acetate crystallized out. 1.3 g (49.5%) of white powder were isolated, m.p. 201°–202° C., $R_F$ 0.28 ($CH_2Cl_2$/MeOH/50% strength acetic acid, 8/2/0.5).

EXAMPLE 5

N-(2-Naphthylsulfonyl)glycylproline (p-amidinobenzyl)amide acetate a) Boc-Glycylproline (p-cyanobenzyl)amide 30 ml of diisopropylethylamine, 10.6 g (40 mmol) of N-(p-cyanobenzyl)prolylamide hydrochloride and 32 ml (44 mmol) of propanephosphonic anhydride (50% strength solution in ethyl acetate) were successively added to a solution of 7.0 g (40 mmol) Boc-glycine in 240 ml of methylene chloride at 0° C. After stirring at 0° C. for 2 h, the organic phase was washed with 1N NaOH, water and saturated NaCl solution, dried and distilled to remove the solvent. 14.8 g (96%) of white powder were isolated, $R_F$=0.57 ($CH_2Cl_2$/MeOH, 9/1).

$^1$H-NMR (DMSO-d$^6$), δ in ppm: 1.4 (s, 9H, (CH$_3$)$_3$), 1.7–2.2 (m, 4H, CH$_2$—CH$_2$), 3.3–3.6 (m, 2H, N—CH$_2$ of proline), 3.8 (m, 2H, N—CH$_2$ of glycine), 4.3–45 (m, 3H, CH and N—CH$_2$—Ar), 6.8 (m, 1H, BOC—) 7.4–7.5 (m (apparent triplet due to second rotamer), 2H, Ar—H), 7.8 (d, 2H, Ar—H) 8.5 and 8.8 (each m, together 1H (two rotamers), NH)

b) H-Glycylproline (p-cyanobenzyl)amide hydrochloride

The Boc group was eliminated from the above compound as in 1b. 8 g (64%) of white powder were isolated.

$^1$H-NMR (DMSO-d$^6$), δ in ppm: 1.7–2.2 (m, 4H, CH$_2$—CH$_2$), 3.4–4.0 (m, 4H, N—CH$_2$—of proline and glycine —), 4.2–4.5 (m, 3H, CH and N—CH$_2$—Ar), 7.5 (d, 2H, Ar), 7.8 (d, 2H, Ar), 8.3 (s, br, 3H, NH$_3^+$), 8.9 and 9.2 (each m, together 1H (two rotamers), NH)

c) N-(2-Naphthylsulfonyl)glycylproline (p-cyanobenzyl)amide

The above compound was reacted with 2-naphthylsulfonyl chloride as in 1c to result in 3.3 g of white powder, R$_F$=0.59 (CH$_2$Cl$_2$/MeOH, 9/1).

$^1$H-NMR (DMSO-d$^6$), δ in ppm: 1.6–2.0 (m, 4H, CH$_2$—CH$_2$), 3.3–3.5 (m, 2H, N—CH$_2$ (proline)), 3.7 (m, 2H, N—CH$_2$ (glycine)), 4.1–4.4 (m, 3H, CH and N—CH$_2$—Ar), 7.4—8.5 (13H, aromatic H and 2NH)

d) N-(2-Naphthylsulfonyl)glycylproline (p-thioamidobenzyl)amide [sic]

The above compound was converted into the thioamide as in 1d.

Yield: 3.0 g (85%) of yellowish powder $^1$H-NMR (DMSO-d$^6$), δ in ppm: 1.5–2.0 (m, 4H, CH$_2$—CH$_2$), 3.3–3.5 (m, 2H, N—CH$_2$ (proline)), 3.7 (m, 2H, N—CH$_2$ (glycine)), 4.1–4.4 (m, 3H, CH and N—CH$_2$—Ar), 9.5 (s, 1H, thioamide), 9.8 (s, 1H, thioamide)

e) N-(2-Naphthylsulfonyl)glycylproline (p-amidinobenzyl) amide acetate

Preparation took place as in 1e. 2.5 g (68%) of hydroiodide, R$_F$=0.09 (CH$_2$Cl$_2$/MeOH, 9 (1) [sic], were isolated and then converted into the acetate using an acetate ion exchanger (Amberlite), HPLC purity 99%. FAB-MS (M-H)$^+$=493.5.

$^1$H-NMR (DMSO-d$^6$), δ in ppm: 1.6–2.0 (m, 4H, CH$_2$—CH$_2$), ~3.5 ((m, 2H, N—CH$_2$ (proline)—partly covered by H$_2$O signal), 3.7 (m, 2H, N—CH$_2$ (glycine)), 4.1–4.4 (m, 3H, CH and N—CH$_2$—Ar), 7.3–8.5 (13H, aromatic H and NH), ~8.4–9.2 (4H, amidine)

EXAMPLE 6

N-(1-Naphthylsulfonyl)glycylproline (p-amidinobenzyl)amide

The title compound was obtained as in Example 5 using 1-naphthylsulfonyl chloride. FAB-MS (M-H)$^+$=493.

EXAMPLE 7

N-(n-Hexadecylsulfonyl)-D-phenylalanylproline (p-amidinobenzyl)amide acetate

Preparation took place as in Example 1, white powder, m.p. 194°–201° C., FAB-MS (M-H)$^+$=695.

EXAMPLE 8

N-(n-Butylsulfonyl)-D-phenylalanylproline (p-amidinobenzyl)amide acetate

Preparation took place as in Example 1, white powder, m.p. 203°–211° C., FAB-MS (M-H)$^+$=526.5.

EXAMPLE 9

N-(Isopropylaminosulfonyl)-D-phenylalanylproline (p-amidinobenzyl)amide acetate a) N-(Isopropylaminosulfonyl)-D-phenylalanylproline (p-cyanobenzyl)amide D-Phenylalanylproline (p-cyanobenzyl)amide hydrochloride was reacted with isopropylaminosulfonyl chloride as in Example 1c.

b) N-(Isopropylaminosulfonyl)-D-phenylalanylproline (p-hydroxyamidinobenzyl)amide This compound was prepared as in Example 4b by reacting 9a with hydroxylamine hydrochloride.

c) N-(Isopropylaminosulfonyl)-D-phenylalanylproline (p-amidinobenzyl)amide acetate 9b was hydrogenated in a methanol/glacial acetic acid/THF solvent mixture with Pd/carbon at 40° C. (13 h). The catalyst was then filtered off with suction, the solution was concentrated under reduced pressure and codistilled with ethanol several times, the residue was taken up in water, the aqueous phase was extracted 3 times with ethyl acetate, and then the aqueous phase, which contained the required product, was lyophilized (white solid, m.p. 199°–205° C., FAB-MS: M+H$^+$: 515).

EXAMPLE 10

N-(Dimethylaminosulfonyl)-D-phenylalanylproline (p-amidinobenzyl)amide acetate

Preparation took place as in Example 9 (white solid, m.p. decomposition above 90° C., FAB-MS: M+H$^+$: 501).

EXAMPLE 11

N-Hydroxysulfonyl-D-phenylalanylproline (p-amidinobenzyl)amide 0.58 g (0.33 ml, 5 mmol) of chlorosulfonic acid in 10 ml of DCM was slowly added dropwise at 20° C. with cooling to a solution of 1.8 g (4.36 mmol) of D-phenylalanylproline (p-cyanobenzyl)amide hydrochloride and 1.68 g (13.0 mmol) of diisopropylethylamine in 20 ml of DCM. After stirring at room temperature for 30 min, the mixture was diluted to 100 ml with DCM and extracted initially with 2M HCl and then twice with 10 ml of water, and the organic phase was dried over magnesium sulfate and evaporated in a rotary evaporator. 2.0 g of N-hydroxysulfonyl-D-phenylalanylproline (p-cyanobenzyl)amide were obtained as crude product which was used for the next reaction without further purification.

2.0 g of said crude product were stirred together with 0.9 g (13 mmol) of hydroxylamine hydrochloride and 2.5 ml of diisopropylamine in 50 ml of ethanol at room temperature overnight and then concentrated, and the volatile constituents were removed at 50° C. under high vacuum in 1 h. The product is very soluble in water, which made workup by extraction impossible. The crude product (1.8 g) was used directly for the following hydrogenation.

The crude product was hydrogenated under a slightly super-atmospheric pressure of hydrogen in a mixture of 40 ml of methanol and 5 ml of glaial acetic acid with a spatula tip of 10% palladium on carbon at 50° C. After 5.5 h, the catalyst was filtered off, and the solution was concentrated in a rotary evaporator and codistilled several times with methanol and toluene. The resulting product was stirred with DCM several times to result in 1.5 g (73% of theory over 3 stages) of pure N-hydroxysulfonyl-D-phenylalanylproline (p-amidinobenzyl)amide, which, according to NMR, was in the form of a betaine. M.p. 220°–224° C., white powder, FAB-MS: 474 (M-H)⁺.

The following compounds were prepared as in Example 4:

EXAMPLE 12

N-Trifluoromethylsulfonyl-D-phenylalanylproline (p-amidinobenzyl)amide acetate

White crystals, m.p. 240°–242° C. (decomposition), FAB-MS: 526 (M-H)⁺.

EXAMPLE 13

N-(β, β, β-Trifluoroethylsulfonyl)-D-phenylalanylproline (p-amidinobenzyl)amide acetate White crystals [sic], m.p. 87°–89° C. (amorphous), FAB-MS: 540 (M-H)⁺.

EXAMPLE 14

N-(n-Octylsulfonyl)-D-phenylalanylproline (p-amidinobenzyl)amide acetate

White amorphous crystals [sic], FAB-MS: 570 (M-H)⁺.

EXAMPLE 15

N-Methylsulfonyl-(D,L)-diphenylalanylproline (p-amidinobenzyl)amide acetate

White amorphous crystals [sic], FAB-MS: 548 (M-H)⁺.

EXAMPLE 16

N-Methylsulfonyl-di(4-chlorophenyl)alanylproline (p-amidinobenzyl)amide acetate

White amorphous crystals [sic], FAB-MS: 617 (M-H)⁺.

EXAMPLE a

Tablets of the following composition are produced in a tablet press in a conventional way:
100 mg of substance of Example 2
240 mg of corn starch
27 mg of gelatin
90 mg of lactose
4.5 mg of Aerosil® (chemically pure silica in submicroscopically fine dispersion)
0.5 mg of magnesium stearate
4.5 mg of talc

EXAMPLE b

Coated tablets of the following composition are produced in a conventional way:
200 mg of substance of Example 3
300 mg of core composition
350 mg of sugar-coating composition
The core composition consists of 9 parts of corn starch, 3 parts of lactose and 1 part of Luviskole VA 64 (60:40 vinylpyrrolidone/vinyl acetate copolymer, cf. Pharm. Ind. (1962) 586). The sugar-coating composition consists of 5 parts of sucrose, 2 parts of corn starch, 2 parts of calcium carbonate and 1 part of talc. The tablets produced in this way are subsequently provided with an enteric coating.

EXAMPLE c 100 g of substance of Example 1 are dissolved in 5,000 ml of water with the addition of NaCl and adjusted to pH 6.0 with 0.1N NaOH to result in a solution which is isotonic with blood. 5 ml portions of this solution are dispensed into ampoules and sterilized.

We claim:

1. A compound of the formula I

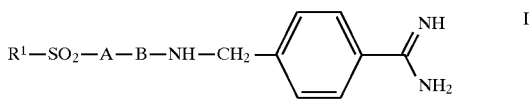

and its stereoisomers and its salts with physiologically tolerated acids, in which the substituents have the following meanings:

$R^1$ is $C_1$–$C_{20}$-alkyl, $C_1$–$C_3$-fluoroalkyl, $C_3$–$C_8$-cycloalkyl, aryl-$C_1$–$C_{10}$-alkyl, aryl, hetaryl, OH or $R^3R^2N$ where $R^2$ and $R^3$ are identical or different and are hydrogen, $C_1$–$C_{10}$-alkyl, aryl, aryl-$C_1$–$C_{10}$-alkyl or together are a $C_2$–$C_7$-alkylene chain to which an aryl or hetaryl radical can be fused or which can contain a hetero atom (O, S, NH or substituted N), A is an α-amino acid residue of the formula II

where $R^4$ is hydrogen, $C_1$–$C_8$-alkyl, $C_3$–$C_7$-cycloalkyl, aryl or aryl-$C_1$–$C_3$-alkyl, $R^5$ is hydrogen, $C_1$–$C_8$-alkyl, $C_3$–$C_7$-cycloalkyl, $C_3$–$C_7$-cycloalkyl-$C_{1-3}$-alkyl, aryl, aryl-$C_1$–$C_3$-alkyl, di($C_3$–$C_7$-cycloalkyl)-methyl or diphenylmethyl or—if $R^4$=H—a $C_1$–$C_8$-alkyl radical in which one hydrogen atom is replaced by $OR^6$ or CO—$OR^6$ ($R^6$=hydrogen, $C_1$–$C_8$-alkyl or aryl-$C_1$–$C_3$-alkyl), or $R^4$ and $R^5$ together are a $C_2$–$C_6$-alkylene chain, which may contain a fused-on aryl radical, B is a cyclic α-amino acid residue of the formula III

where m is 2, 3 or 4, and one hydrogen on the ring can be replaced by a hydroxyl or $C_1$–$C_3$-alkyl group and—if m=3 or 4—a $CH_2$ group in the ring can be replaced by oxygen, sulfur, NH— or N—$C_1$–$C_4$-alkyl and/or two adjacent hydrogen atoms can be replaced by a double bond.

2. A pharmaceutical composition comprising the compound of claim 1 and a pharmaceutically acceptable carrier.

3. A method of treating a patient in need of thrombin-inhibiting activity, which comprises administering to said patient an effective amount of the composition of claim 2.

4. The method of claim 3, wherein the patient is suffering from a condition selected from myocardial infarct, peripheral arterial occlusive disease, deep vein thrombosis, pulmonary embolism and stroke.

5. A method of preventing reocclusion in a patient after opening of an arterial vessel by mechanical methods or lysis, which comprises administering to the patient an effective amount of the composition of claim 2.

* * * * *